United States Patent
Zarbel et al.

(10) Patent No.: US 12,193,836 B2
(45) Date of Patent: Jan. 14, 2025

(54) DEVICES, SYSTEMS AND METHODS FOR NON-INVASIVE MEASUREMENT OF BLOOD ALCOHOL LEVEL

(71) Applicants: Dor Zarbel, Moshav Balfouria (IL); Rahav Raviv, Gedera (IL); Shiri Carmielli, Ness Ziona (IL)

(72) Inventors: Dor Zarbel, Moshav Balfouria (IL); Rahav Raviv, Gedera (IL); Shiri Carmielli, Ness Ziona (IL)

(73) Assignee: DYM SENSE LTD., Tel Aviv-Jaffa (IL)

( * ) Notice: Subject to any disclaimer, the term of this patent is extended or adjusted under 35 U.S.C. 154(b) by 871 days.

(21) Appl. No.: 17/062,077

(22) Filed: Oct. 2, 2020

(65) Prior Publication Data
US 2021/0100498 A1 Apr. 8, 2021

Related U.S. Application Data

(60) Provisional application No. 62/909,851, filed on Oct. 3, 2019.

(51) Int. Cl.
*A61B 5/00* (2006.01)
*A61B 5/1172* (2016.01)
(Continued)

(52) U.S. Cl.
CPC .......... *A61B 5/4845* (2013.01); *A61B 5/0059* (2013.01); *A61B 5/1172* (2013.01);
(Continued)

(58) Field of Classification Search
CPC ...... B60K 28/06; B60K 28/063; B60K 28/02; B60K 28/066; B60R 25/102; B60R 25/04;
(Continued)

(56) References Cited

U.S. PATENT DOCUMENTS 4,738,333 A * 4/1988 Collier ............... A61B 5/18
340/576
4,996,161 A * 2/1991 Conners ............ G01N 33/4972
340/576

(Continued)

FOREIGN PATENT DOCUMENTS

CN 203142402 8/2013
CN 107031653 3/2018

OTHER PUBLICATIONS

Office Action U.S. Appl. No. 17/258,457 mailed on Jul. 1, 2021.
(Continued)

*Primary Examiner* — Paul N Dickson
*Assistant Examiner* — Caitlin Anne Miller
(74) *Attorney, Agent, or Firm* — PEARL COHEN ZEDEK LATZER BARATZ LLP

(57) ABSTRACT

A system for determining a blood alcohol level of a subject may include a single light-emitting diode (LED) or, in some embodiments, two LEDs that may be operated in a pulsed mode and may illuminate a target location on a subject (e.g., a portion of a distal phalanx of a finger) with multiple illuminated light pulses. The system may include a photosensor that may sense multiple light pulses received from (e.g., reflected from, or transmitted through) the target location and generate multiple output signals. The system may include a controller that may determine a blood alcohol level of the subject based on the multiple output signals. Utilization of a single LED/two LEDs and operation thereof in a pulsed mode may prevent (or significantly reduce) heating of the LED(s) and/or the photosensor, thus eliminating a need in cooling units.

8 Claims, 11 Drawing Sheets

(51) Int. Cl.
*A61B 5/1455* (2006.01)
*A61B 5/18* (2006.01)
*B60K 28/02* (2006.01)
*G06V 40/12* (2022.01)

(52) U.S. Cl.
CPC .............. *A61B 5/1455* (2013.01); *A61B 5/18* (2013.01); *A61B 5/6826* (2013.01); *B60K 28/02* (2013.01); *G06V 40/12* (2022.01)

(58) Field of Classification Search
CPC .. B60R 25/252; G01N 2201/062; A61B 5/18; A61B 5/0059; A61B 5/4845; A61B 5/6826; A61B 2010/0009
USPC .................................................. 180/272, 287
See application file for complete search history.

(56) References Cited

U.S. PATENT DOCUMENTS

| | | | | |
|---|---|---|---|---|
| 5,348,003 | A * | 9/1994 | Caro | A61B 5/6826 |
| | | | | 702/30 |
| 5,424,545 | A * | 6/1995 | Block | A61B 5/1455 |
| | | | | 250/341.7 |
| 5,743,349 | A * | 4/1998 | Steinberg | B60K 28/063 |
| | | | | 180/272 |
| 5,823,951 | A * | 10/1998 | Messerschmidt | A61B 5/14532 |
| | | | | 514/937 |
| 6,157,317 | A | 12/2000 | Walker | |
| 6,229,908 | B1 * | 5/2001 | Edmonds, III | G01N 33/4972 |
| | | | | 356/442 |
| 6,504,614 | B1 | 1/2003 | Messerschmidet et al. | |
| 6,654,125 | B2 | 11/2003 | Maynard et al. | |
| 6,885,439 | B2 * | 4/2005 | Fujieda | G06V 40/1394 |
| | | | | 382/116 |
| 6,967,581 | B2 * | 11/2005 | Karsten | B60K 28/063 |
| | | | | 340/576 |
| 7,016,713 | B2 | 3/2006 | Gardner et al. | |
| 7,403,804 | B2 | 7/2008 | Ridder et al. | |
| 7,451,852 | B2 | 11/2008 | Stewart et al. | |
| 7,812,712 | B2 * | 10/2010 | White | B60R 25/241 |
| | | | | 340/426.2 |
| 8,095,193 | B2 * | 1/2012 | Ridder | A61B 5/0071 |
| | | | | 340/576 |
| 8,297,399 | B2 * | 10/2012 | Goi | B60K 28/063 |
| | | | | 340/576 |
| 8,469,134 | B2 * | 6/2013 | Osaki | B60T 7/14 |
| | | | | 340/576 |
| 8,515,506 | B2 | 8/2013 | Ridder et al. | |
| 8,581,711 | B2 * | 11/2013 | Morgan | B60K 28/063 |
| | | | | 340/426.11 |
| 8,781,544 | B2 * | 7/2014 | Al-Ali | A61B 5/6826 |
| | | | | 600/323 |
| 9,475,387 | B2 | 10/2016 | Wu | |
| 10,034,635 | B2 * | 7/2018 | Nothacker | A61B 5/097 |
| 10,045,096 | B2 * | 8/2018 | Briggs | A61B 5/00 |
| 10,099,554 | B2 * | 10/2018 | Steeg | A61B 5/1455 |
| 10,441,176 | B2 * | 10/2019 | Islam | G01J 3/28 |
| 2004/0239510 | A1 | 12/2004 | Karsten | |
| 2006/0212195 | A1 | 9/2006 | Veith et al. | |
| 2009/0092296 | A1 * | 4/2009 | Yokoyama | G06V 40/1318 |
| | | | | 455/556.1 |
| 2010/0108425 | A1 | 5/2010 | Crespo | |
| 2012/0075094 | A1 | 3/2012 | Keays | |
| 2012/0242469 | A1 | 9/2012 | Morgan | |
| 2013/0169442 | A1 | 7/2013 | Ruocco | |
| 2014/0359722 | A1 | 12/2014 | Schultz | |
| 2017/0096145 | A1 * | 4/2017 | Bahn | B60Q 9/00 |
| 2017/0263120 | A1 | 9/2017 | Durie, Jr. et al. | |

OTHER PUBLICATIONS

US Office action of U.S. Appl. No. 17/258,457 mailed on Jul. 9, 2021.
International Search Report of Application No. PCT/IL2019/050752 mailed on Oct. 10, 2019.

* cited by examiner

DEVICES, SYSTEMS AND METHODS FOR NON-INVASIVE MEASUREMENT OF BLOOD ALCOHOL LEVEL

CROSS REFERENCE TO RELATED APPLICATION

This application claims priority from U.S. Provisional Patent Application No. 62/909,851, filed Oct. 3, 2019, which is hereby incorporated by reference in its entirety.

FIELD OF THE INVENTION

The present invention relates to the field of measurement of blood alcohol level and, more particularly, to optical systems therefor.

BACKGROUND OF THE INVENTION

Some current commercially available optical systems for determining a blood alcohol level utilize arrays of multiple light-emitting diodes (LEDs) that are operated in a constant power mode and include one or more cooling units for cooling the system. As a result, such systems may have relatively large dimensions, may be relatively expensive, and may require a preset time in order to be ready for measurement.

SUMMARY OF THE INVENTION

One aspect of the present invention may provide a system for determining a blood alcohol level of a subject. The system may include a single light-emitting diode (LED) or, in some embodiments, two LEDs, that may be operated in a pulsed mode and may illuminate a target location on a subject (e.g., a portion of a distal phalanx of a finger, or a distal interphalangeal joint) with multiple illuminated light pulses. The system may include a photosensor that may sense multiple light pulses received from (for example, reflected from, or, in some embodiments, transmitted through) the target location and that may generate multiple output signals. The system may include a controller including a processing unit that may determine a blood alcohol level of the subject based on at least a portion of the multiple output signals.

In some embodiments, the system may be installed in a vehicle, and the controller may be capable of determining at least one of a blood alcohol level of a subject, an identity of the subject and a subject's driving fitness condition. The determined subject's driving fitness condition may be indicative of whether the subject is fit or is unfit to drive the vehicle. In various embodiments, the controller may be capable of enabling a fit subject to drive the vehicle and/or of preventing an unfit subject from driving the vehicle.

Another aspect of the present invention may provide a method of determining a subject's driving fitness condition. The method may include determining an identity of a subject, performing a real-time verification of the subject, determining a blood alcohol level of the subject, and determining a subject's driving fitness condition based on at least the determined blood alcohol level of the subject, the determined identity of the subject and a predetermined dataset of driving fitness conditions, wherein the determined subject's driving fitness condition is indicative of whether the subject is fit or is unfit to drive a vehicle.

In some embodiments, the method may include generating a notification concerning the determined subject's driving fitness condition. In some embodiments, the method may include preventing the subject from driving the vehicle when the determined subject's driving fitness condition indicates that the driver is not fit to drive the vehicle. In various embodiments, the method may include enabling a fit subject to drive the vehicle and/or of preventing an unfit subject from driving the vehicle.

Some embodiments of the present invention may provide a system for determining a subject's driving fitness condition, the system including: a housing; a light emitting diode (LED) supported by the housing and configured to illuminate a target location of the subject with multiple illuminated light pulses; a photosensor supported by the housing and configured to sense multiple light pulses received from the target location of the subject and to generate corresponding multiple output signals; and a controller including a processing unit, wherein the controller is configured to determine a blood alcohol level of the subject based on at least a portion or the multiple output signals.

In some embodiments, the controller is configured to determine the subject's driving fitness condition based on the determined blood alcohol level of the subject and a predetermined dataset of driving fitness conditions.

In some embodiments, the system further includes a vehicle interface, wherein the controller is configured to control the vehicle via the vehicle interface based on the determined subject's driving fitness condition to allow a fit subject to drive the vehicle and to prevent an unfit subject from driving the vehicle.

In some embodiments, the system further includes a touch verification sensor configured to generate touch verification sensor output signal, and wherein the controller is configured to verify, based on at least a portion of the touch verification sensor output signal, that the subject is continuously touching at least one component of the system during the determination of the blood alcohol level.

In some embodiments, the system further includes a vehicle interface, wherein the controller is configured to control the vehicle via the vehicle interface to allow the subject to drive the vehicle if the verification is successful and to prevent the subject from driving the vehicle if the verification is not successful.

In some embodiments, the touch verification sensor is an oxygen saturation optical sensor.

In some embodiments, the controller is configured to: determine at least one physiological parameter of the subject based on the touch verification sensor output signal; and determine the blood alcohol level of the subject further based on the determined at least one physiological parameter.

In some embodiments, the system further includes a fingerprint sensor configured to obtain a fingerprint pattern of the subject, and wherein the controller is configured to: determine an identity of the subject based on the obtained fingerprint pattern and a reference fingerprint patterns dataset; and determine the subject's driving fitness condition further based on at least one of the determined identity of the subject and a predetermined authorized subjects dataset.

In some embodiments, the LED is emitting light of a wavelength ranging between 1900-2600 nm.

In some embodiments, a time duration of at least some of the multiple illuminated light pulses ranges between 5-50 µs.

In some embodiments, a time offset between at least some of subsequent illuminated light pulses of the multiple illuminated light pulses ranges between 5-50 µs.

In some embodiments, the housing includes a cavity for receiving the target location of the subject, wherein the LED and the photosensor are on opposite sides of the cavity with respect to each other.

In some embodiments, the housing includes a cavity for receiving the target location of the subject, wherein the LED and the photosensor are on a first side of the cavity, and wherein the system includes a light reflector on a second side of the cavity that is opposite to the first side thereof.

In some embodiments, the system includes a second LED supported by the housing and configured to illuminate a target location of the subject with second multiple illuminated light pulses, wherein: the photosensor is configured to sense second multiple light pulses received from the target location of the subject and to generate corresponding multiple second output signals; and the controller is configured to determine the blood alcohol level of the subject further based on at least a portion or the multiple second output signals.

In some embodiments, the controller is configured to control the LED and the second LED to alternately illuminate the respective target location.

In some embodiments, the LED and the second LED are capable of emitting light having at least partly overlapping wavelength ranges.

In some embodiments, the LED and the second LED are capable of emitting light having not overlapping wavelength ranges.

In some embodiments, the LED and the second LED are configured to illuminate the same target location of the subject.

In some embodiments, the LED and the second LED are configured to illuminate different target locations of the subject.

In some embodiments, the system includes a second photosensor, wherein the housing includes a cavity for receiving the target location of the subject, and wherein the LED and the photosensor are on a first side of the cavity and the second LED and the second photosensor are on a second side of the cavity that is opposite to the first side thereof.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and in order to show how the same can be carried into effect, reference will now be made, purely by way of example, to the accompanying drawings in which like numerals designate corresponding elements or sections throughout.

In the accompanying drawings.

Figure 1A:
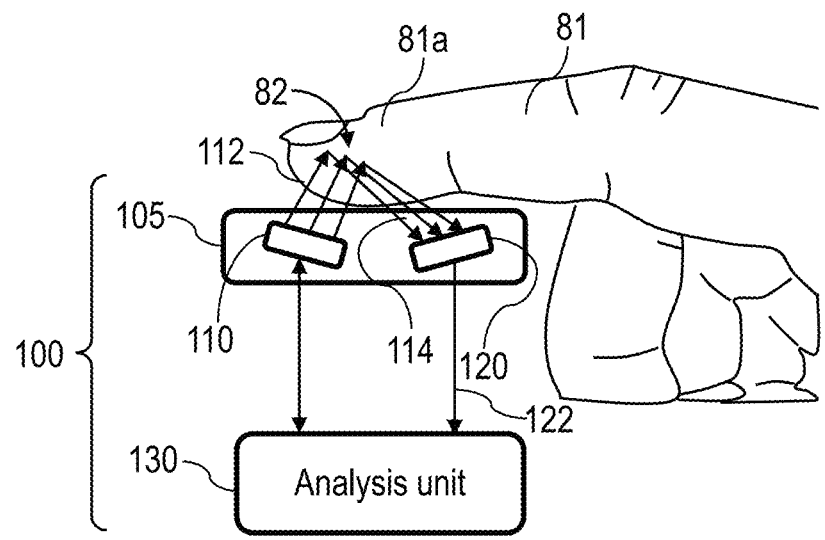
FIG. 1A is a schematic illustration of a system for determining a blood alcohol level of a subject, according to some embodiments of the invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor or a microprocessor.

Some embodiments of the present invention may provide a system for determining a blood alcohol level of a subject. The system may include a single light-emitting diode (LED) or, in some embodiments, two LEDs that may be operated in a pulsed mode and may illuminate a target location on a subject (e.g., a portion of a distal phalanx of a finger) with multiple illuminated light pulses. The system may include a photosensor that may sense multiple reflected light pulses received from (for example, reflected from, or, in some embodiments, transmitted through) the target location and that may generate multiple output signals. The system may include a controller including a processing unit that may determine a blood alcohol level of the subject based on the multiple output signals.

Advantageously, utilization of a single LED, or, in some embodiments, of two LEDs, and operation thereof in a pulsed mode may prevent (or significantly reduce) heating of the LED(s) and/or of the photosensor and may thus eliminate a need in a cooling unit. In this manner, the disclosed system may be smaller and cheaper as compared to some current commercially available systems that typically utilize arrays of multiple LEDs in a constant power mode and include one or more cooling units for cooling thereof. The disclosed system needs no stabilization means and does not require any preparation time prior to performing the measurement. The disclosed system may be capable of providing a measurement result within a time interval of up to 5 seconds.

In some embodiments, the system may be installed in a vehicle, and the controller may be capable of determining at least one of a blood alcohol level of a subject, an identity of the subject and a subject's driving fitness condition. The determined subject's driving fitness condition may be indicative of whether the subject is fit or is unfit to drive the vehicle. The controller may be capable of enabling a fit subject to drive the vehicle and/or of preventing an unfit subject from driving the vehicle.

Reference is now made to FIG. 1A, which is a schematic illustration of a system 100 for determining a blood alcohol level of a subject, according to some embodiments of the invention.

According to some embodiments, system 100 may include a housing 105, at least one light-emitting diode (LED) 110, a photosensor 120 and a controller 130.

Figure 1B:
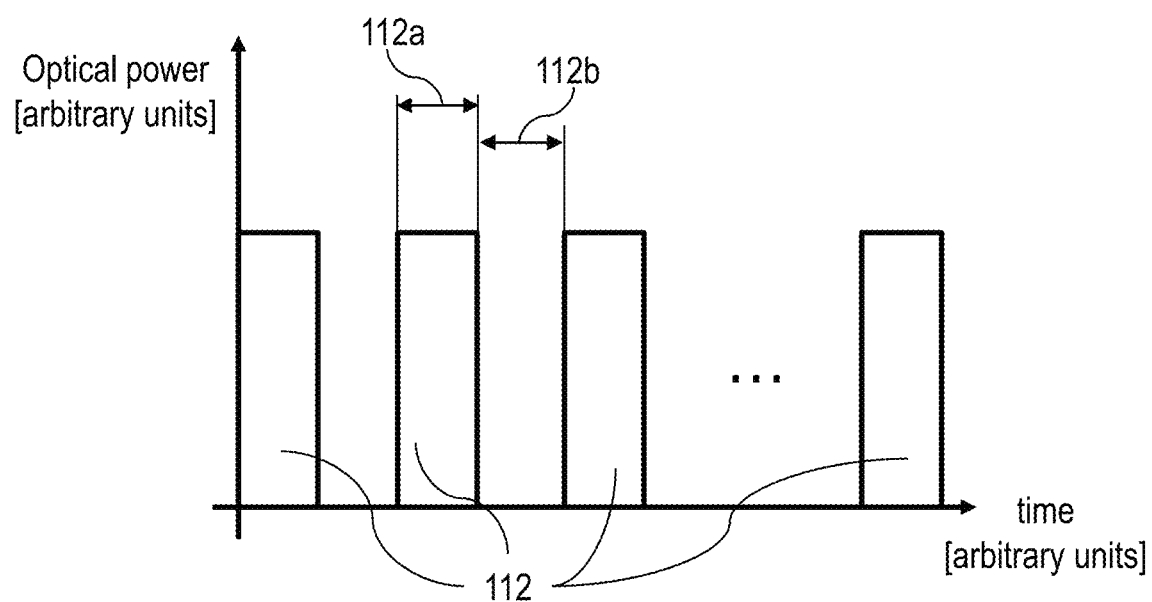
FIG. 1B is a graph illustrating multiple illuminated light pulses generatable by a light-emitting diode (LED) of a system for determining a blood alcohol level of a subject, according to some embodiments of the invention.
Figure 1C:
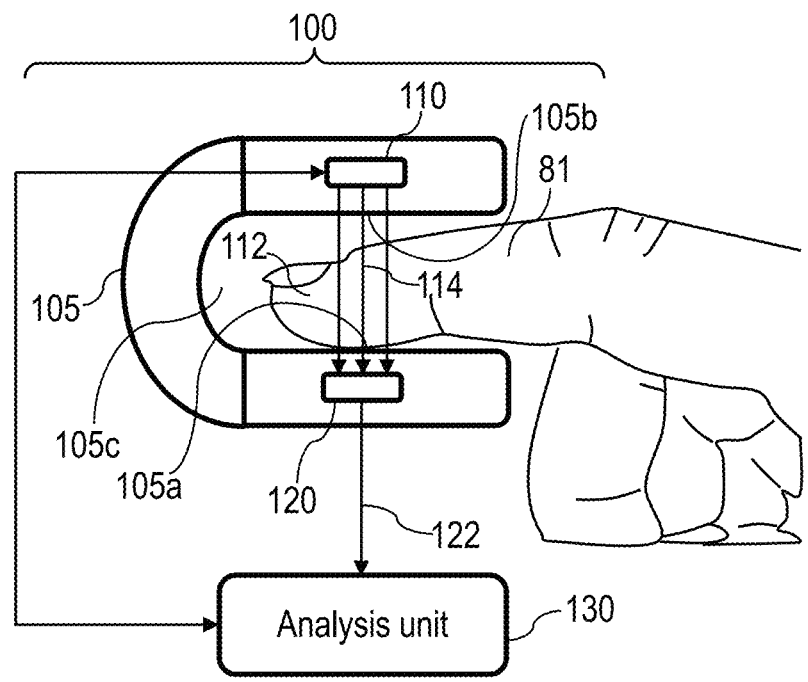
FIGS. 1C and 1D are schematic illustrations of various arrangements of a light-emitting diode (LED) and a photosensor of a system for determining a blood alcohol level of a subject, according to some embodiments of the invention.
Figure 1D:
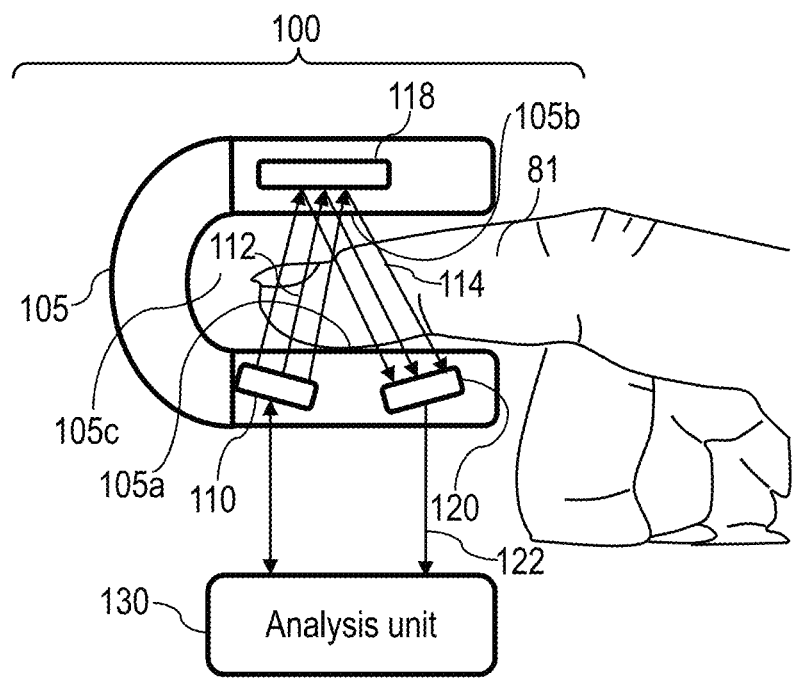

In some embodiments, system 100 may include a single LED 110 (e.g., as shown in FIGS. 1A, 1C and 1D). LED 110 may illuminate a target location 82 of a subject with multiple illuminated light pulses 112. In some embodiments, LED 110 may generate light of a wavelength ranging between 1900-2600 nm.

Target location 82 may be, for example, a portion of a distal phalanx 81a of a finger 81 of the subject.

Photosensor 120 may sense multiple light pulses 114 received from (e.g., reflected from or, in some embodiments, transmitted through) target location 82 and may generate multiple output signals 122. For example, each of the multiple output signals 122 may correspond to one of multiple light pulses 114 that may correspond to one of multiple illuminated light pulses 112.

LED 110 and photosensor 120 may be supported by housing 105. Housing 105 may have different shapes, depending on a relative position of LED 110 and photosensor 120. In embodiments shown in FIG. 1A, housing 105 has a flat (or substantially flat) shape.

Controller 130 may include a processing unit. Controller 130 may receive multiple output signals 122 from photosensor 120. Controller 130 may determine a blood alcohol level of the subject based on multiple output signals 122.

Embodiments shown in FIG. 1A may be easy for utilization in various systems. For example, system shown in FIG. 1A may be installed on a start button in a vehicle. Furthermore, in system shown in FIG. 1A light 112, 114 may travel relatively short distance, which may result in stronger output signals 122.

Reference is now made to FIG. 1B, which is a graph illustrating multiple illuminated light pulses 112 generatable by a light-emitting diode (LED) 110 of a system 100 for determining a blood alcohol level of a subject, according to some embodiments of the invention.

In some embodiments, a time duration 112a of at least some of multiple illuminated light pulses 112 may range between 5-50 μs. In some embodiments, a time offset 112b between at least some of subsequent illuminated light pulses 112 may range between 5-50 μs. In some embodiments, a LED current may range between 0.1-1 A.

Reference is now made to FIGS. 1C and 1D, which are schematic illustrations of various arrangements of a light-emitting diode (LED) 110 and a photosensor 120 of a system 100 for determining a blood alcohol level of a subject, according to some embodiments of the invention.

In various embodiments, LED 110 and photosensor 120 may be arranged in various positions with respect to each other. The relative position of LED 110 and photosensor 120 may, for example, dictate the shape of housing 105.

For example, in embodiments shown in FIG. 1C, housing 105 may include a cavity 105c for receiving target location 82 of the subject (e.g., housing 105 may have a substantially U-shape), wherein LED 110 and photosensor 120 may be at opposite sides 105a, 105b of cavity 105c. In embodiments shown in FIG. 1C, a measurement is performed in substantially closed cavity 105c so as interference of light 112, 114 with an ambient light may be substantially eliminated or significantly reduced. Embodiments shown in FIG. 1C may provide measurement through the entire thickness of target location 82 of the subject.

In another example, in embodiments shown in FIG. 1D, LED 110 and photosensor 120 may be at the same side 105a of cavity 105c. In embodiments shown in FIG. 1D, system 100 may include a light reflector 118 on side 105b of cavity 105c, wherein side 105b is opposite to side 105a.

In embodiments shown in FIG. 1D, a measurement is performed in substantially closed cavity 105c so as interference of light 112, 114 with an ambient light may be substantially eliminated or significantly reduced. In embodiments shown in FIG. 1D light 112, 114 may travel twice through the entire thickness of target location 82 of the subject. In embodiments shown in FIG. 1D, electric connections may be only on one side of housing 105 (e.g., on side 105a).

It is noted that other relative positions of LED 110 and photosensor 120 are also possible.

Figure 1E:
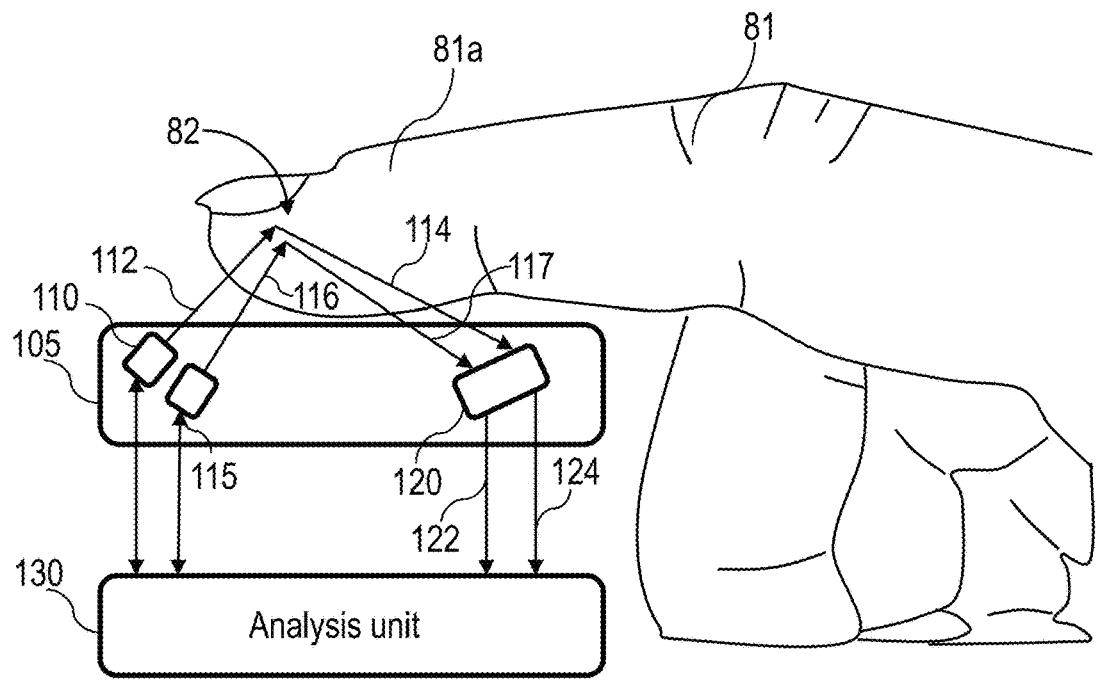
FIG. 1E is a schematic illustration of a system for determining a blood alcohol level of a subject and including two light-emitting diodes, according to some embodiments of the invention.

Reference is now made to FIG. 1E, which is a schematic illustration of a system 100 for determining a blood alcohol level of a subject including two light-emitting diodes, according to some embodiments of the invention.

According to some embodiments, system 100 may include a first LED 110 (e.g., as described above with respect to FIGS. 1A, 1C and 1D) and a second LED 115.

In some embodiments, first LED 110 and second LED 115 may emit light of the same (or substantially the same) wavelength. For example, first LED 110 and second LED 115 may emit light having a wavelength of 1900-2600 nm.

In some embodiments, first LED 110 may emit light of a wider wavelength range than second LED 115. For example, first LED 110 may emit light having a wavelength of 1900-2600 nm, and second LED 115 may emit light having a wavelength of 2300-2400 nm.

In some embodiments, first LED 110 and second LED 115 may emit light of different and not overlapping wavelengths. In some embodiments, first LED 110 and second LED 115 may emit light of at least partly overlapping wavelengths.

In some embodiments, first LED 110 and second LED 115 may be arranged to illuminate the same target location 82 on, for example, finger 81 of the subject (e.g., as shown in FIG. 1E). In some embodiments, first LED 110 and second LED 115 may be arranged to illuminate different target locations on, for example, finger 81 of the subject.

In some embodiments, first LED 110 and second LED 115 may be disposed on the same side of housing 105 (e.g., as shown in FIG. 3A). In some embodiments, first LED 110 and second LED 115 may be disposed on opposite sides of housing 105.

First LED 110 may illuminate target location 82 on finger 81 of the subject with first multiple illuminated light pulses 112. Second LED 115 may illuminate target location 82 on finger 81 of the subject (or a different target location on finger 81) with second multiple illuminated light pulses 116.

In some embodiments, controller 130 may control first LED 110 and second LED 115 to alternately illuminate the respective target location. In this manner, interference between first multiple illuminated light pulses 112 and second multiple illuminated light pulses 116 may be avoided. In some other embodiments, controller 130 may control first LED 110 and second LED 115 to simultaneously illuminate the respective target location.

Photosensor 120 may sense (e.g., alternately or simultaneously) first multiple light pulses 114 and second multiple light pulses 117 received from (for example, reflected from, or in some embodiments, transmitted through) the respective target location (e.g., and sourced in first multiple illuminated light pulses 112 and second multiple illuminated light pulses 116, respectively) and may generate corresponding multiple first output signals 122 and multiple second output signals 124, respectively.

Controller 130 may receive multiple first output signals 122 and multiple second output signals 124 from photosensor 120. Controller 130 may determine a blood alcohol level of the subject based on multiple first output signals 122 and multiple second output signals 124.

Embodiments shown in FIG. 1E may be easy for utilization in various systems. For example, system shown in FIG. 1E may be installed on a start button in a vehicle. Furthermore, in system shown in FIG. 1E light 112, 114 may travel relatively short distance, which may result in stronger output signals 122. Embodiments shown in FIG. 1E may benefit from an advantage of using two LEDs 110, 115.

Figure 1F:
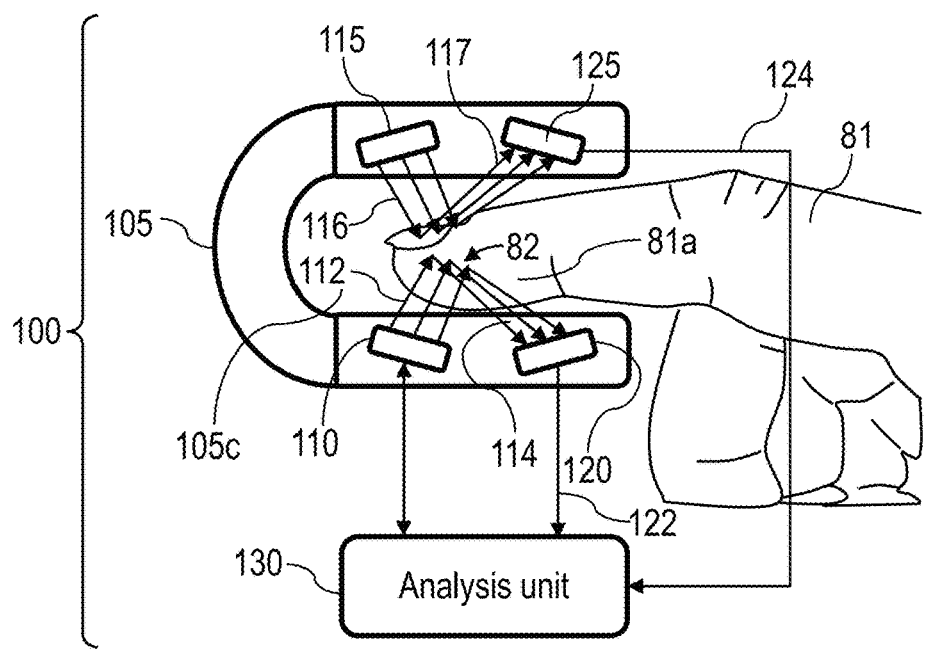
FIG. 1F is a schematic illustration of a system for determining a blood alcohol level of a subject and including two light-emitting diodes and two photosensors, according to some embodiments of the invention.

Reference is now made to FIG. 1F, which is a schematic illustration of a system 100 for determining a blood alcohol level of a subject and including two light-emitting diodes and two photosensors, according to some embodiments of the invention.

According to some embodiments, system 100 may include a first photosensor 120 and a second photosensor 125. In some embodiments, first LED 110 and first photosensor 120 may be on side 105a, and second LED 115 and second photosensor 125 may be on side 105b of cavity 105c of housing 105, wherein side 105b is opposite to side 105a (e.g., as shown in FIG. 1F).

In embodiments shown in FIG. 1F, first photosensor 120 and second photosensor 125 may sense first multiple light pulses 114 and second multiple light pulses 117 received from (for example, reflected from or, in some embodiments, transmitted through) the respective target location (e.g., and sourced in first multiple illuminated light pulses 112 and second multiple illuminated light pulses 116, respectively, from first LED 110 and second LED 115, respectively) and may generate corresponding multiple first output signals 122 and multiple second output signals 124, respectively.

Advantageously, the disclosed system for determining a blood alcohol level of a subject may utilize a single LED, or two LEDs, being operated in a pulsed mode. Specifically, LED(s) may provide pulses of a peak optical power for a short time duration, which prevents (or significantly reduces) heating of the LED(s) and/or of photosensor(s). In this manner, the system does not require cooling of the LED(s) and/or of photosensor(s). Accordingly, the disclosed system may be smaller and cheaper than some current commercially available systems that typically utilize LED arrays (e.g., including multiple LEDs) in a constant power mode and include one or more cooling units for cooling thereof.

In embodiments shown in FIG. 1F, a measurement is performed in substantially closed cavity 105c so as interference of light 112, 114, 116, 117 with an ambient light may be substantially eliminated or significantly reduced. Furthermore, in system shown in FIG. 1F, light 112, 114, 116, 117 may travel relatively short distance, which may result in stronger output signals 122, 124. Embodiments shown in FIG. 1F may benefit from an advantage of using two LEDs 110, 115.

Figure 2A:
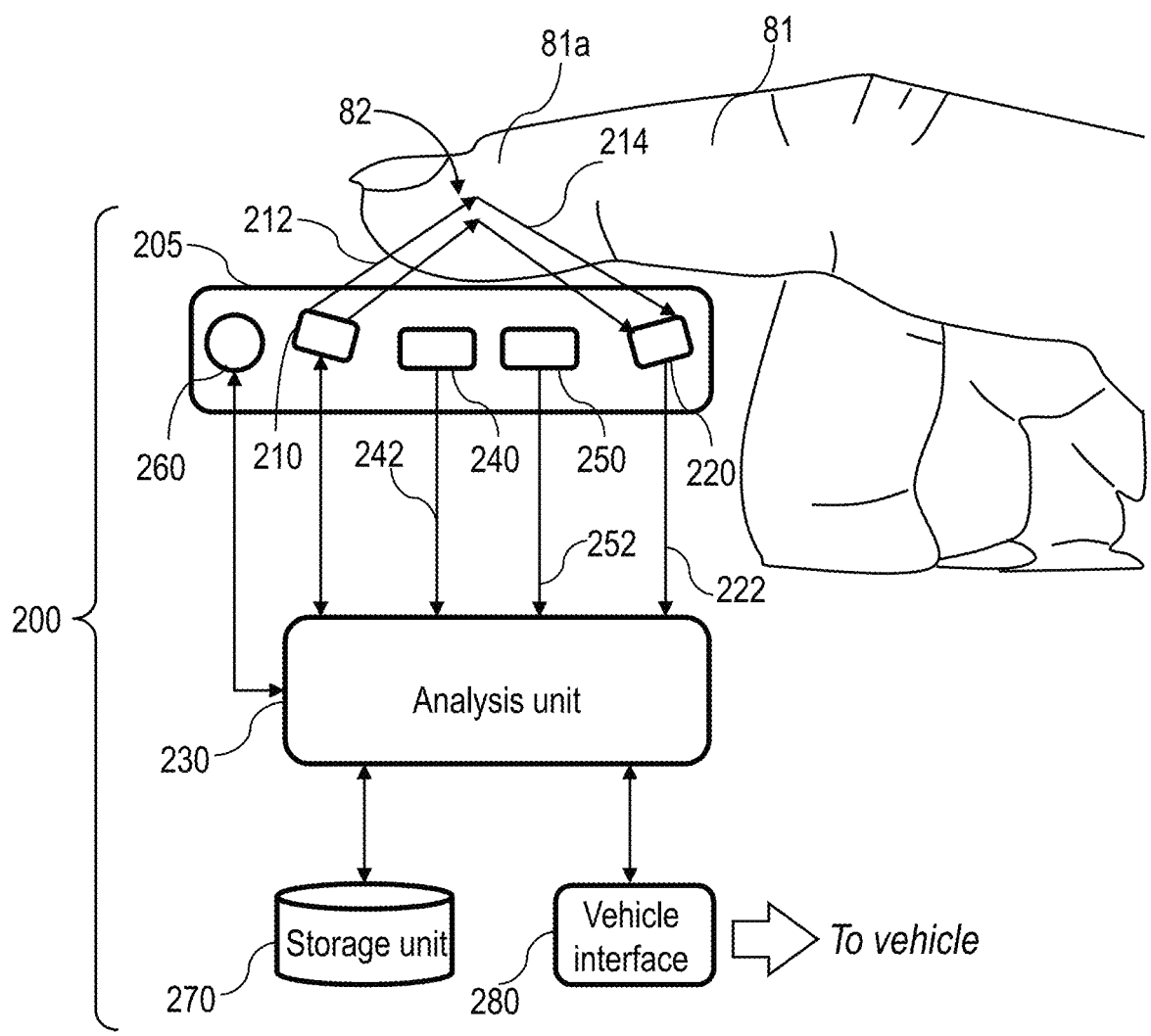
FIG. 2A is a schematic illustration of a system for determining a subject's driving fitness condition, according to some embodiments of the invention.

Reference is now made to FIG. 2A, which is a schematic illustration of a system 200 for determining a subject's driving fitness condition, according to some embodiments of the invention.

According to some embodiments, system 200 may be installed in a vehicle and may be capable of determining at least a blood alcohol level of a subject and of a subject's driving fitness condition at least based on the determined blood alcohol level thereof.

According to some embodiments, system 200 may include a housing 205, at least one light-emitting diode (LED) 210, a photosensor 220 and a controller 230. For example, housing 205, LED 210, photosensor 220 and controller 230 may be similar to housing 105, LED 110, photosensor 120 and controller 130, respectively, as described above with respect to FIGS. 1A, 1C, 1D, 1E and 1F.

According to some embodiments, system 200 may include a single LED 210 (e.g., as shown in FIG. 2A and as described above with respect to FIGS. 1A, 1C and 1D). In some other embodiments, system 200 may include two LEDs and/or two photosensors (e.g., as described above with respect to FIGS. 1E and 1F).

LED 210 may illuminate a target location 82 on a subject with multiple illuminated light pulses 212. Photosensor 220 may sense multiple light pulses 214 received from (for example, reflected from, or, in some embodiments, transmitted through, target location 82) and may generate multiple output signals 222. For example, each of the multiple output signals 222 may correspond to one of multiple reflected light pulses 214 that may correspond to one of multiple illuminated light pulses 212. LED 210 and photosensor 220 may be disposed within housing 205.

Controller 230 may include a processing unit. Controller 230 may receive multiple output signals 222 from photosensor 220. Controller 230 may determine a blood alcohol level of the subject based on at least a portion of multiple output signals 222 (e.g., as described above with respect to FIG. 1A).

According to some embodiments, system 200 may include a fingerprint sensor 240. Fingerprint sensor 240 may be supported by housing 205 and may be in communication with controller 230. Fingerprint sensor 240 may obtain a fingerprint pattern 242 of the subject.

Controller 230 may receive fingerprint pattern 242 from fingerprint sensor 240. Controller 230 may determine an identity of the subject, based on fingerprint pattern 242 and based on a reference fingerprint patterns dataset. The reference fingerprint patterns dataset may be stored in, for example, a storage unit 270 that may be in communication with controller 230.

According to some embodiments, system 200 may include a vehicle interface 280. Vehicle interface 280 may be in communication with controller 230 and in communication with the vehicle.

In some embodiments, controller 230 may control the vehicle via vehicle interface 280 according to the determined identity of the subject and a predetermined authorized subject's dataset. For example, controller 230 may allow an authorized subject to drive the vehicle and/or prevent an unauthorized subject from driving the vehicle. The predetermined authorized subject's dataset may be stored in storage unit 270.

In some embodiments, controller 230 may store the determined blood alcohol level for the determined identity of the subject in storage unit 270. In this manner, a log of the determined blood alcohol level for each of the subjects may be generated.

According to some embodiments, system 200 may include a touch verification sensor 250. Touch verification sensor 250 may be supported by housing 205 and may be in communication with controller 230. Touch verification sensor 250 may generate touch verification sensor output signal 252.

Controller 230 may receive touch verification sensor output signal 252 from touch verification sensor 250. Controller 230 may perform real-time subject's verification based on touch verification sensor output signal 252. For example, the real-time subject's verification may enable the system to ensure that the subject does not replace its finger 81 with, for example, any other object (e.g., that does not contain alcohol) or with a finger of another person upon identification thereof.

For example, touch verification sensor 250 may be an oxygen saturation optical sensor. In this example, touch verification sensor output signal 252 may be indicative of an oxygen saturation in finger 81 of the subject.

In some embodiments, controller 230 may determine at least one physiological parameter for the subject based on touch verification sensor output signal 252. For example, when touch verification sensor 250 is an oxygen saturation optical sensor, controller 230 may, for example, determine a heartbeat rate of the subject. Controller 230 may determine the blood alcohol level of the subject based on multiple output signals 222 and further based on the determined at least one physiological parameter.

According to some embodiments, controller 230 may determine a subject's driving fitness condition based on at least one of the blood alcohol level of the subject, the determined identity of the subject and a predetermined dataset of driving fitness conditions. The determined subject's driving fitness condition may be indicative of whether the subject is fit or is unfit to drive a vehicle. The predetermined dataset of driving fitness conditions may be stored in storage unit 270. The predetermined dataset of driving fitness conditions may, for example, include identity of at least one driver, weight of the at least one driver, age of the at least one driver, regulation requirements relating to the allowed blood alcohol levels in at least one country, etc.

In some embodiments, controller 230 may generate a notification concerning the determined subject's driving fitness condition. The notification may be, for example, visual, sound, or voice notification. For example, system 200 may include an indicator 260. Indicator 260 may be disposed in housing 205 and may be in communication with controller 230. Indicator 260 may, for example, emit green light when the subject is fit to drive the vehicle or red light when the subject is unfit to drive the vehicle. It is noted that other ways of indication are also possible.

In various embodiments, controller 230 may control the vehicle via vehicle interface 280 according to the determined subject's driving fitness condition to thereby allow a fit subject to drive the vehicle or prevent an unfit subject from driving the vehicle. For example, controller 230 may prevent (e.g., using vehicle interface 280) unfit subject from switching on the vehicle.

Figure 2B:
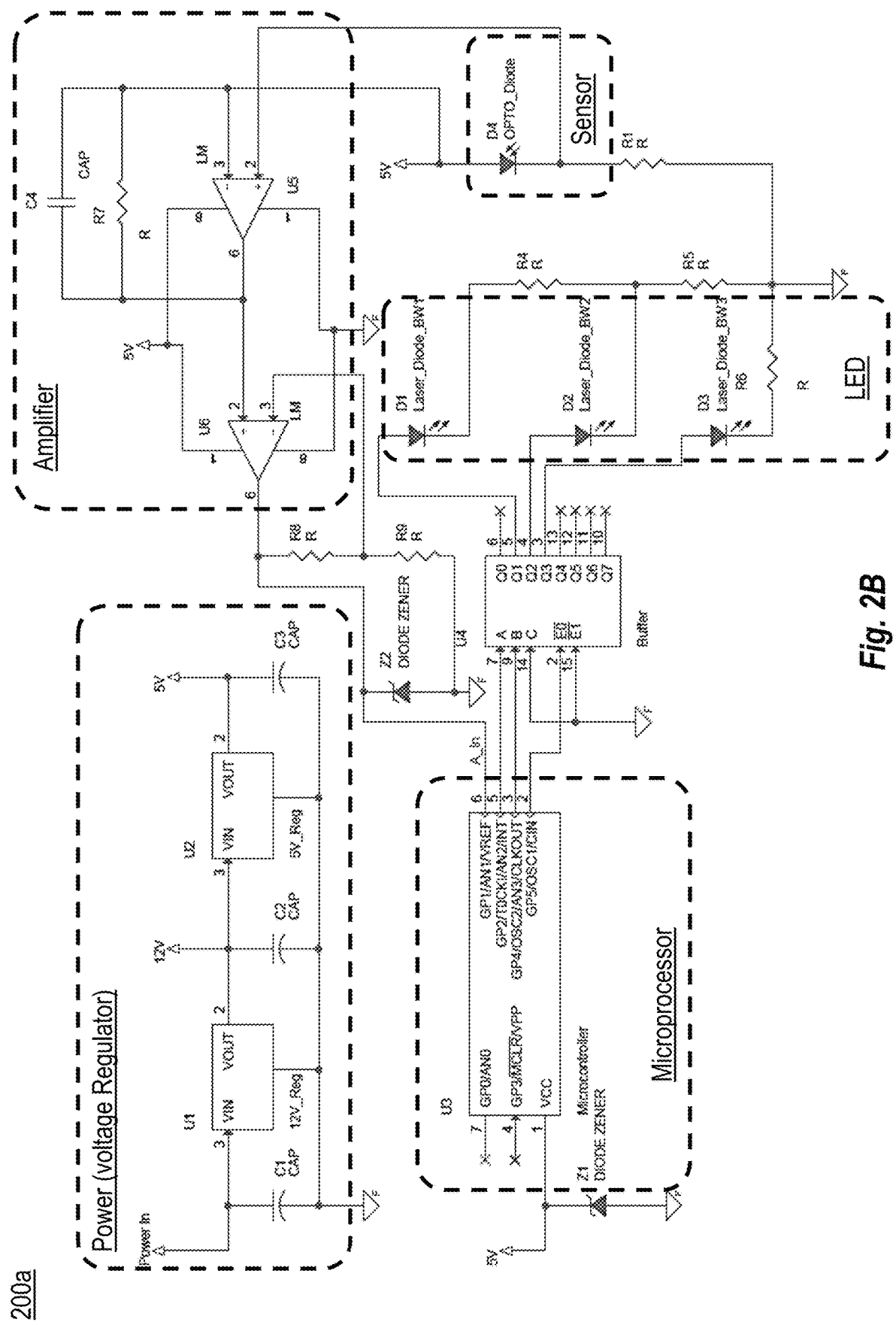
FIG. 2B is a schematic block diagram of an electronic circuitry of a system for determining a blood alcohol level of a subject and capable of determining a subject's driving fitness condition, according to some embodiments of the invention.

Reference is now made to FIG. 2B, which is a schematic block diagram 200a of an electronic circuitry of a system 200 for determining a blood alcohol level of a subject and capable of determining a subject's driving fitness condition, according to some embodiments of the invention.

According to some embodiments, the electronic circuitry of system 200 may include an input voltage regulator, measurement and microcontroller voltage regulator, microcontroller and its peripherals components including all needing protections, memory unit (e.g., may be embedded in the microcontroller), LEDs buffer and current stabilizer (e.g., if needed to support the pulse mode operation of the LEDs), amplifier for the photosensor output signals, fingerprint sensor electronics unit and components, communication components into the car system (e.g., the vehicle interface, may, for example, be different according to customer or application needs), casing. Other configurations of electronic circuitry of system 200 are also possible.

Figure 3:
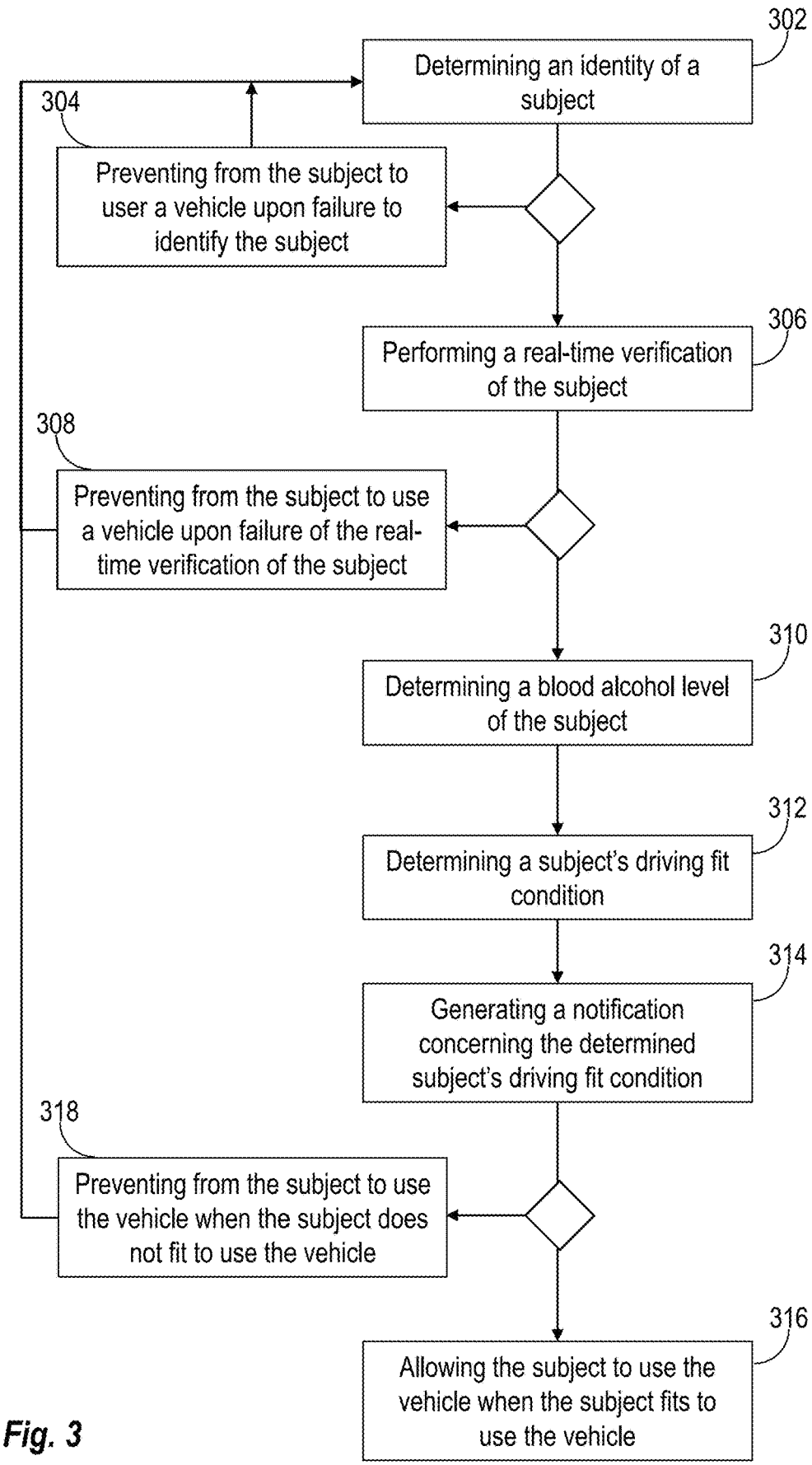
FIG. 3 is a flowchart of a method of determining a subject's driving fitness condition, according to some embodiments of the invention.

Reference is now made to FIG. 3, which is a flowchart of a method of determining a subject's driving fitness condition, according to some embodiments of the invention.

The method may be implemented by system 200 described above with respect to FIG. 2. It is noted that the method is not limited to the flowcharts illustrated in FIG. 3 and to the corresponding description. For example, in various embodiments, the method need not move through each illustrated box or stage, or in exactly the same order as illustrated and described.

Some embodiments may include determining an identity of a subject (stage 302). For example, a fingerprint pattern of the subject may be obtained using a fingerprint sensor and the obtained fingerprint pattern may be compared to a reference fingerprint patterns dataset to thereby determine the identity of the subject (e.g., as described above with respect to FIG. 2).

Some embodiments may include preventing the subject from driving a vehicle upon failure to identify the subject (stage 304). Some embodiments may include repeating stage 402 upon failure to identify the subject.

Some embodiments may include performing a real-time verification of the subject (stage 306). For example, the real-time verification may be performed by measuring a heartbeat of the subject using a heartbeat sensor such as, e.g., oxygen saturation optical sensor (e.g., as described above with respect to FIG. 2).

Some embodiments may include preventing the subject from driving a vehicle upon failure of the real-time verification of the subject (stage 308). Some embodiments may include repeating stage 402 upon failure of the real-time verification of the subject.

Some embodiments may include determining a blood alcohol level of the subject (stage 310). For example, the blood alcohol level of the subject may be determined based on light emitted by a single LED or by two LEDs and reflected from/transmitted through a target location on the subject (e.g., a distal phalanx of the finger) and sensed by a photosensor (e.g., e.g., as described above with respect to FIGS. 1A, 1B, 1C, 1D, 1E, 1F and FIG. 2A).

Some embodiments may include determining a subject's driving fitness condition based on at least the determined blood alcohol level of the subject, the determined identity of the subject and a predetermined dataset of driving fitness conditions, wherein the determined subject's driving fitness condition is indicative of whether the subject is fit or is unfit to drive a vehicle (stage 312). For example, as described above with respect to FIG. 2.

Some embodiments may include generating a notification concerning the determined subject's driving fitness condition (stage 314). For example, using indicator 260 as described above with respect to FIG. 2

Some embodiments may include allowing the subject to drive the vehicle when the determined subject's driving fitness condition indicates that the driver is fit to drive the vehicle (stage 316).

Some embodiments may include preventing the subject from driving the vehicle when the determined subject's driving fitness condition indicates that the driver is not fit to drive the vehicle (stage 318).

Reference is now made to FIGS. 4A, 4B, 4C, 4D, 4E, 4F and 4G, which are graphs depicting experimental results, according to some embodiments of the invention.

FIGS. 4A, 4B, 4C, 4D, 4E, 4F and 4G depict experimental results performed by a system for determining an alcohol blood level of a subject, such as system 100, as described above with respect to FIGS. 1A, 1B, 1C, 1D, 1E and 1F.

Figure 4A:
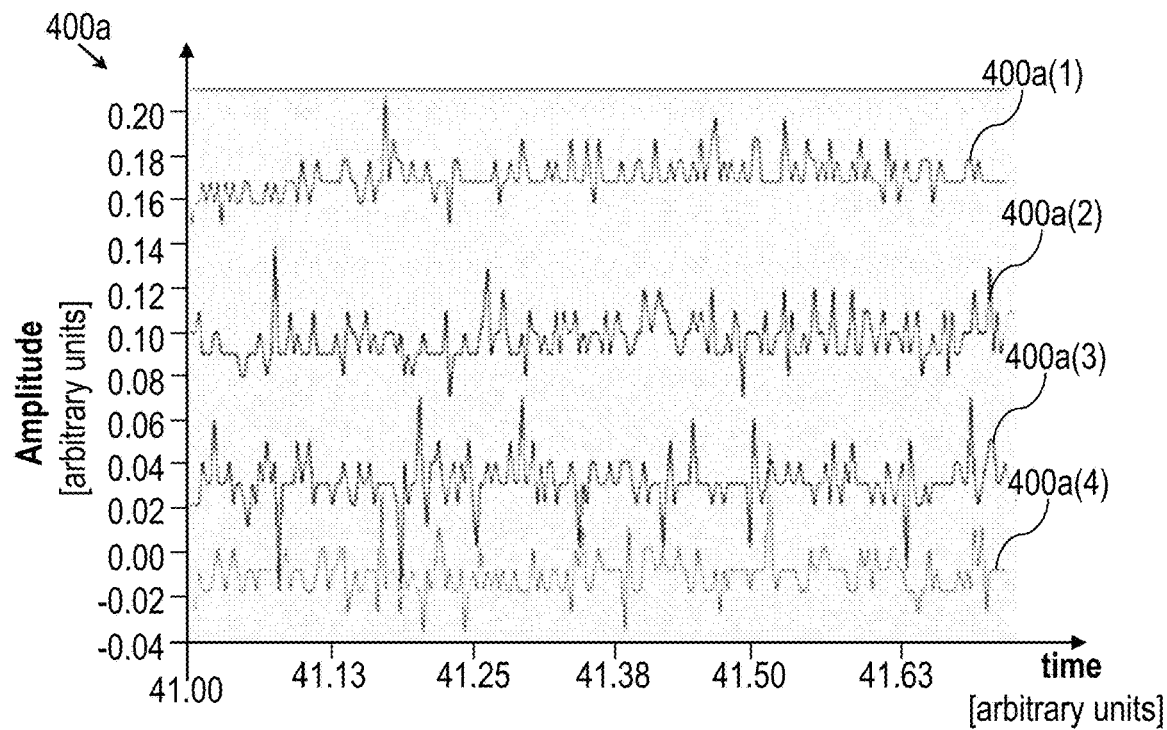
FIGS. 4A, 4B, 4C, 4D, 4E, 4F and 4G, which are graphs depicting experimental results, according to some embodiments of the invention.

FIG. 4A depicts a graph 400a of photosensor output signals 400a(1), 400a(2), 400a(3) and 400a(4) generated based on light pulses received from a distal phalanx of a subject and sourced in multiple illuminated light pulses generated by LEDs of different wavelengths. Each of signals 400a(1), 400a(2), 400a(3) and 400a(4) in FIG. 4A represents a different LED having a different peak wavelength. Lines 400a(1) and 400a(3) represent LEDs having a wavelength of 2200-2290 nm. Lines 400a(2) and 400a(4) represent LEDs having a wavelength of 2300-2390 nm.

Figure 4B:
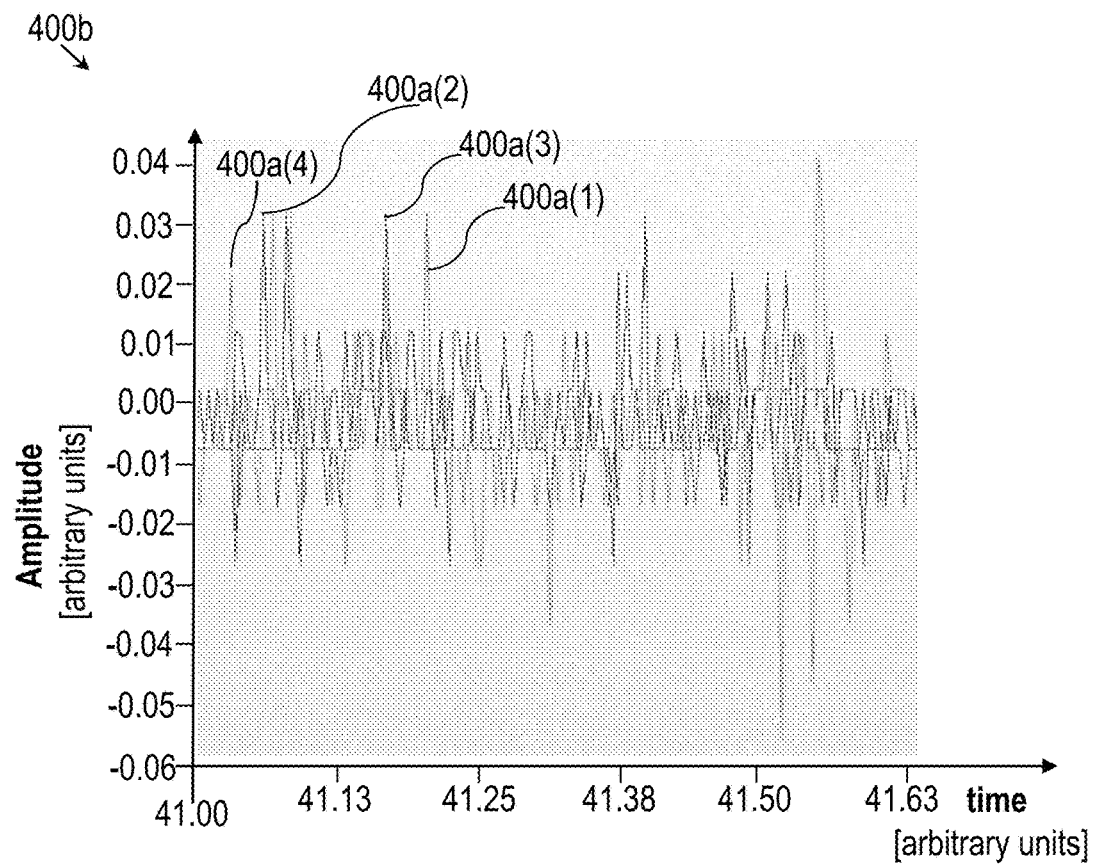

FIG. 4B depicts a graph 400b of photosensor output signals 400a(1), 400a(2), 400a(3) and 400a(4) shown in FIG. 4A as compared to the noise. The multiple received light pulses are notable as compared to noise.

Figure 4C:
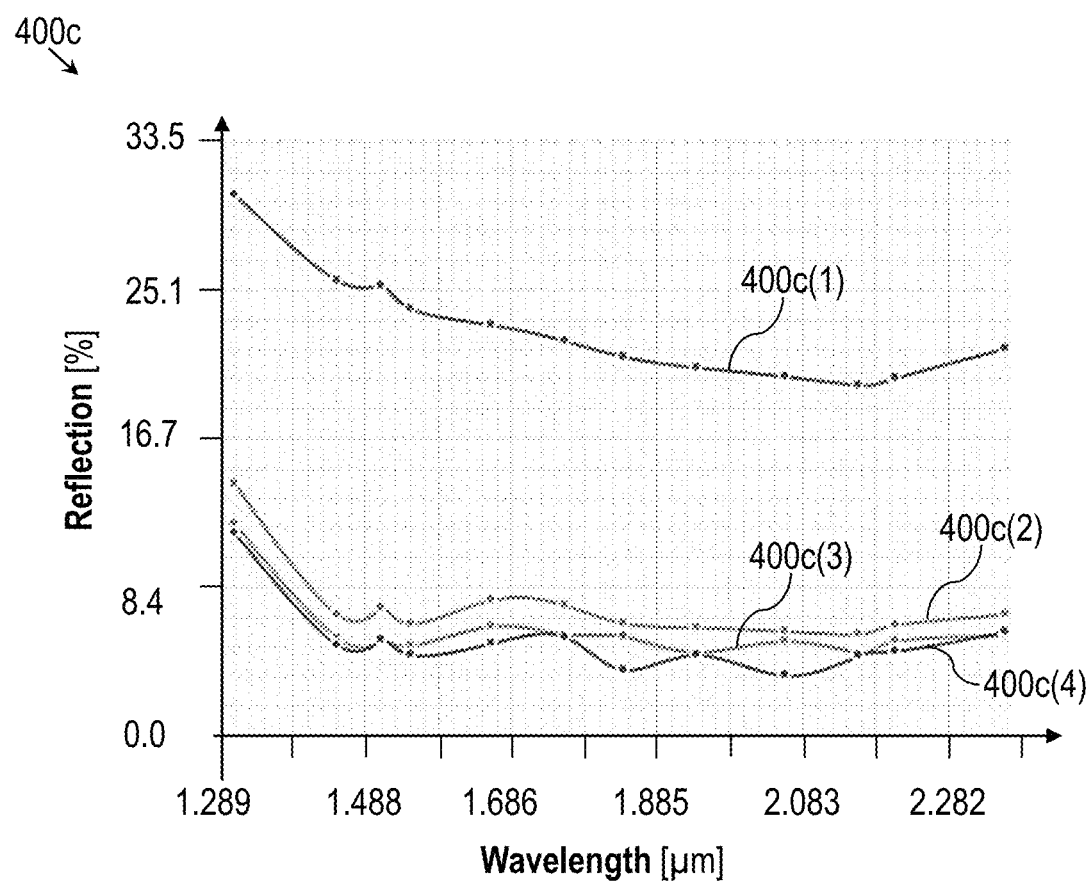

FIG. 4C depicts a graph 400c of measurement results performed by a mini spectrophotometer. Line 400c(1) depicts measurement results for a reference material provided with the spectrophotometer, and lines 400c(2), 400c(3), 400c(4) depict measurement results for different target locations along the distal phalanx of the finger of the subject for different LEDs having different wavelength.

Figure 4D:
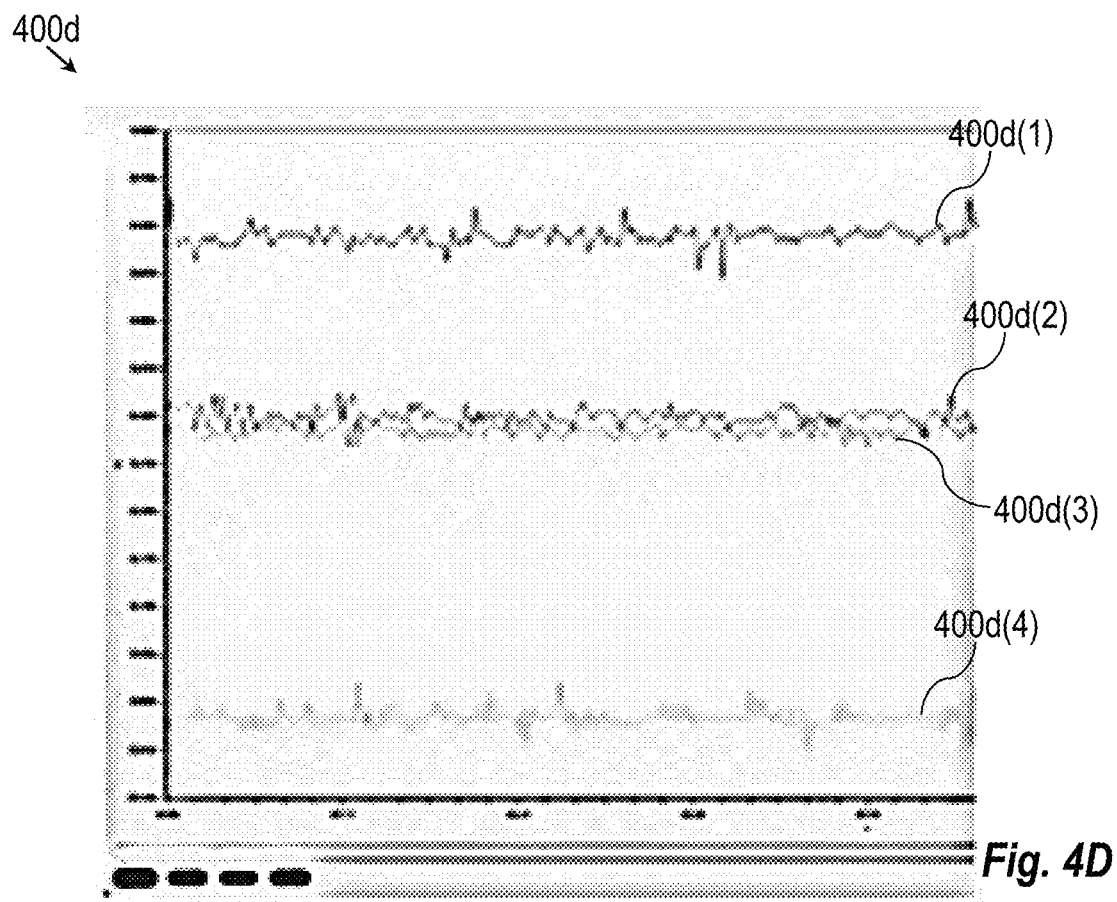
Figure 4E:
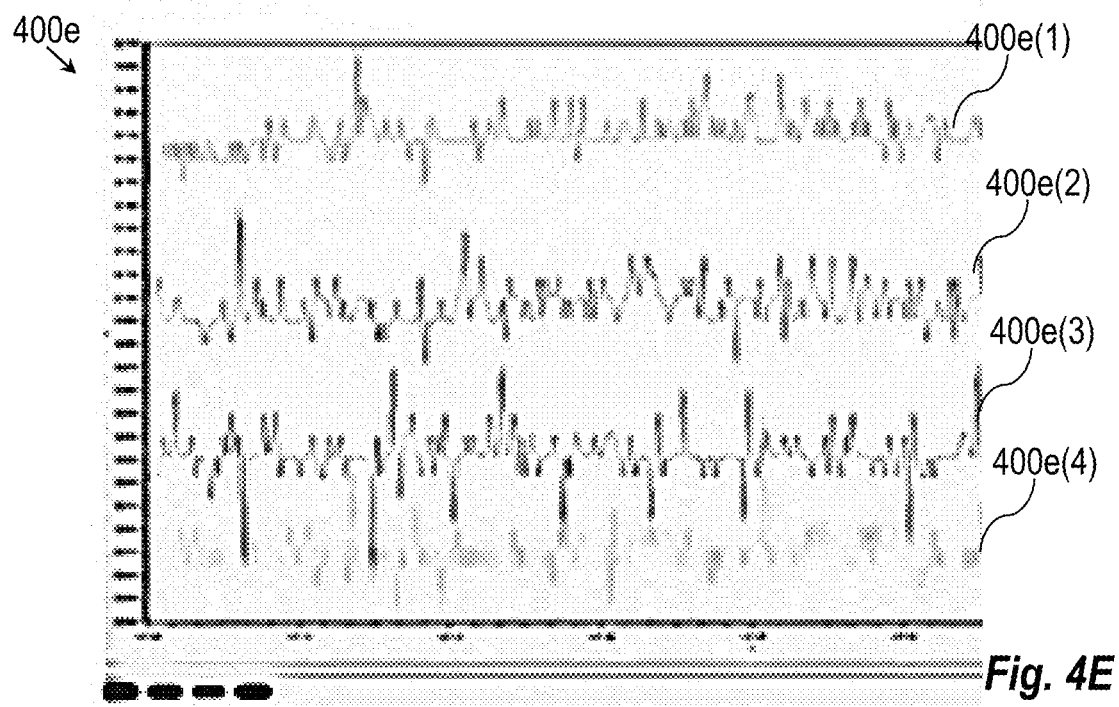

FIGS. 4D and 4E depict graphs 400d and 400e, respectively, of measurement results obtained using the system for determining an alcohol blood level of a subject (such as system 100). FIG. 4D depicts measurement results obtained for the reference material provided with the spectrophotometer, and FIG. 4E depicts measurement results obtained for the distal phalanx of the finger, wherein different signals 400d(1), 400d(2), 400d(3), 400d(4) in FIG. 4D and 400e(1), 400e(2), 400e(3), 400e(4) in FIG. 4E represent different LEDs having different wavelengths.

Figure 4F:
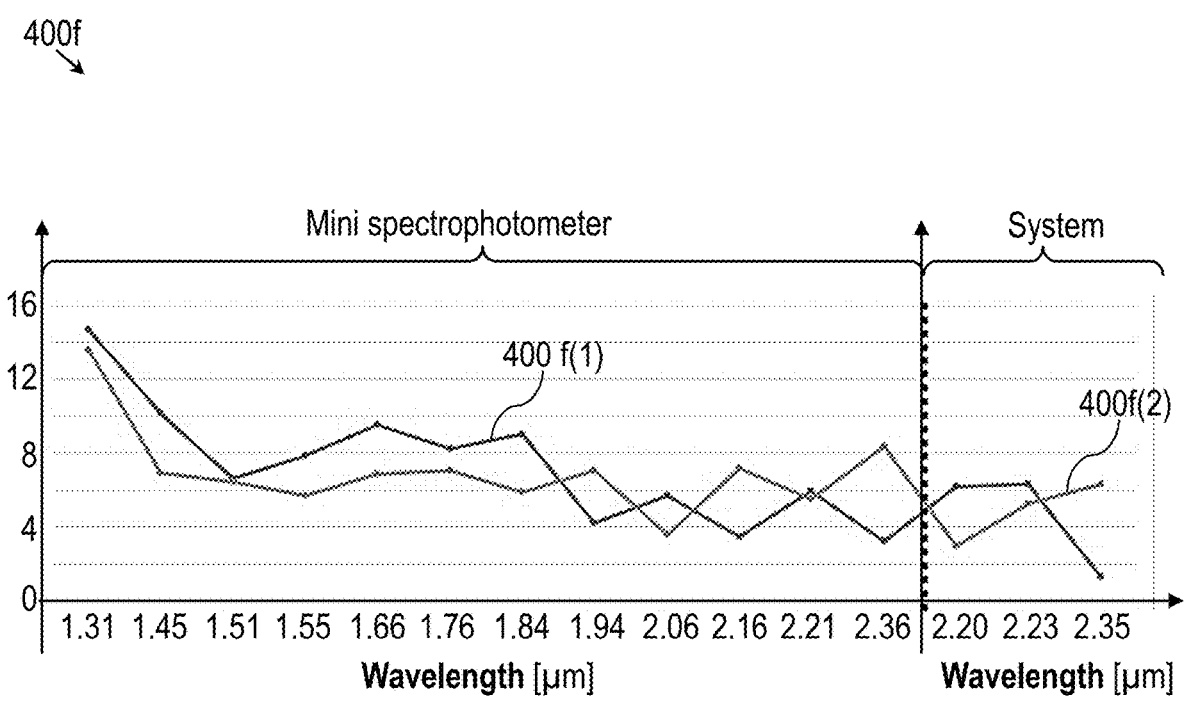

FIG. 4F depicts a graph 400f of measurement results obtained using the system for determining an alcohol blood level of a subject (such as system 100) as compared to measurement results obtained using the mini spectrophotometer. Water (line 400f(2)) was used as a baseline, and alcohol 70% (line 400f(1)) was used as a measured material. It may be noted that alcohol 70% resulted in higher absorption of the light emitted by different LEDs as compared to the baseline. It may be noted that LED having a wavelength of 2350 nm and having a widest effective wavelength range provides the best result.

Figure 4G:
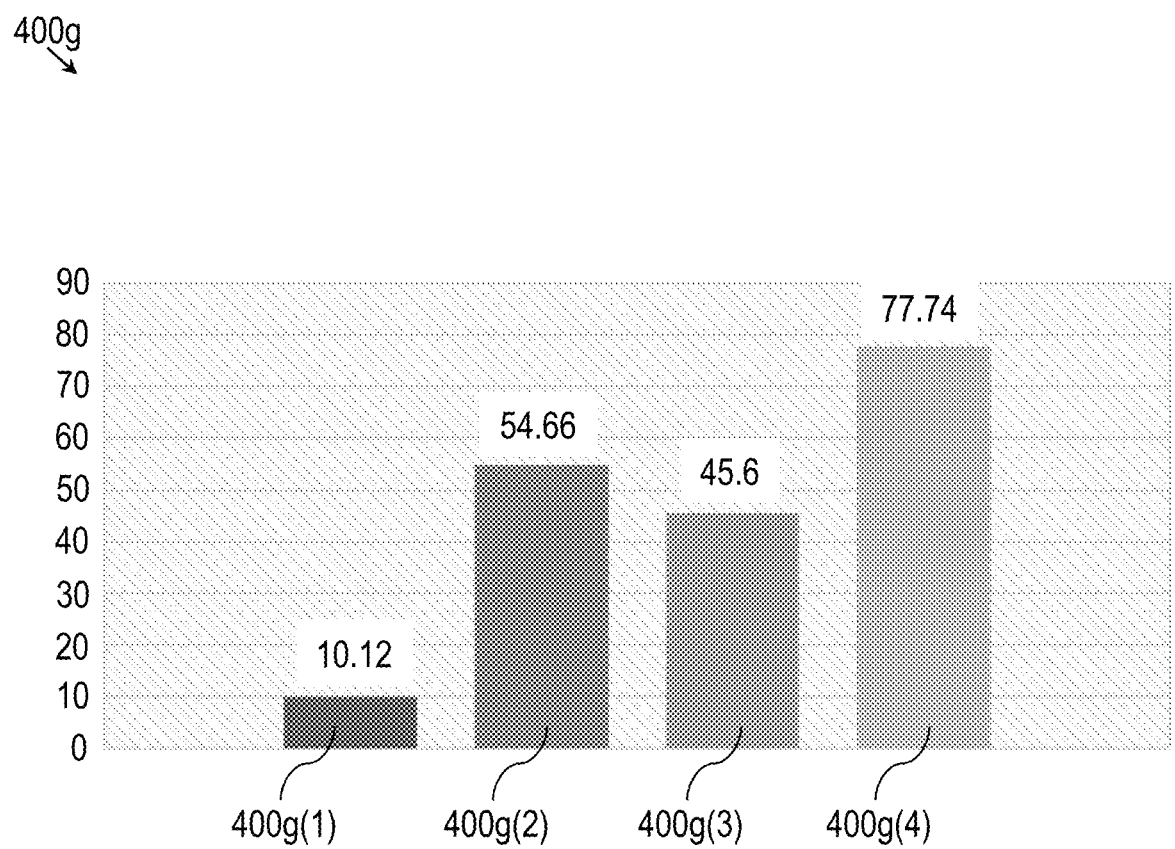

FIG. 4G depicts a graph 400g depicting absorption of the light emitted by the LED having a wavelength of 2350 nm for different materials (empty—bar 400g(1), water—bar 400g(2), sugar water—bar 400g(3) and alcohol 70%-bar 400g(4)). It may be noted that alcohol 70% provides higher absorption values then other tested materials.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system for determining a subject's driving fitness condition, the system comprising:
   a housing;
   a light emitting diode (LED) supported by the housing and configured to illuminate a target location of the subject with multiple illuminated light pulses, wherein a time duration of at least some of the multiple illuminated light pulses ranges between 5-50 µs, and wherein a time offset between at least some of subsequent illuminated light pulses of the multiple illuminated light pulses ranges between 5-50 µs;
   a second LED supported by the housing and configured to illuminate a target location of the subject with second multiple illuminated light pulses, wherein the LED and the second LED are configured to emit light having at least partly overlapping wavelength ranges, and wherein the second LED is configured to emit light having a wavelength range of 2200-2400 nanometers, wherein the LED and the second LED are configured to illuminate different target locations of the subject;
   a photosensor supported by the housing and configured to sense multiple light pulses received from a first target location of the different target locations of the subject and to generate corresponding multiple output signals;
   a second photosensor configured to sense second multiple light pulses received from a second target location of the different target locations of the subject and to generate corresponding multiple second output signals, wherein the housing comprises a cavity for receiving the target location of the subject, and wherein the LED and the photosensor are on a first side of the cavity and the second LED and the second photosensor are on a second side of the cavity that is opposite to the first side thereof;
   an oxygen saturation sensor; and
   a controller comprising a processing unit, wherein the controller is configured to determine at least one physiological parameter of the subject based on a signal generated by the oxygen saturation optical sensor, the at least one physiological parameter comprising a heartbeat rate, wherein the controller is configured to determine a blood alcohol level of the subject based on; at least a portion of the multiple output signals, at least a portion or the multiple second output signals, and the determined at least one physiological parameter, and wherein the controller is configured to determine the subject's driving fitness condition based on the determined blood alcohol level of the subject and a predetermined dataset of driving fitness conditions.

2. The system of claim 1, further comprising a vehicle interface, wherein the controller is configured to control the vehicle via the vehicle interface based on the determined subject's driving fitness condition to allow a fit subject to drive the vehicle and to prevent an unfit subject from driving the vehicle.

3. The system of claim 1, further comprising a touch verification sensor configured to generate touch verification sensor output signal, wherein the controller is configured to verify, based on at least a portion of the touch verification sensor output signal, that the subject is continuously touching at least one component of the system during the determination of the blood alcohol level.

4. The system of claim 3, further comprising a vehicle interface, wherein the controller is configured to control the vehicle via the vehicle interface to allow the subject to drive the vehicle if the verification is successful and to prevent the subject from driving the vehicle if the verification is not successful.

5. The system of claim 1, further comprising a fingerprint sensor configured to obtain a fingerprint pattern of the subject, wherein the controller is configured to:
   determine an identity of the subject based on the obtained fingerprint pattern and a reference fingerprint patterns dataset; and determine the subject's driving fitness condition further based on at least one of the determined identity of the subject and a predetermined authorized subjects dataset.

6. The system of claim 1, wherein the LED is emitting light of a wavelength ranging between 1900-2600 nm.

7. The system of claim 1, wherein:
the photosensor is configured to sense second multiple light pulses received from the target location of the subject and to generate corresponding multiple second output signals; and
the controller is configured to determine the blood alcohol level of the subject further based on at least a portion or the multiple second output signals.

8. The system of claim 7, wherein the controller is configured to control the LED and the second LED to alternately illuminate the respective target location.

* * * * *